United States Patent [19]

Mueller et al.

[11] 4,203,908
[45] May 20, 1980

[54] MANUFACTURE OF CYCLIC ETHERS

[75] Inventors: Herbert Mueller, Frankenthal; Otto H. Huchler, Limburgerhof, both of Fed. Rep. of Germany

[73] Assignee: BASF Aktiengesellschaft, Fed. Rep. of Germany

[21] Appl. No.: 942,654

[22] Filed: Sep. 15, 1978

[30] Foreign Application Priority Data

Sep. 27, 1977 [DE] Fed. Rep. of Germany ....... 2743345

[51] Int. Cl.$^2$ .......................................... C07D 307/08
[52] U.S. Cl. .............................. 260/346.11; 260/333; 260/345.1
[58] Field of Search ................ 260/333, 345.1, 346.11

[56] References Cited

FOREIGN PATENT DOCUMENTS

| | | |
|---|---|---|
| 700036 | 11/1940 | Fed. Rep. of Germany . |
| 711709 | 9/1941 | Fed. Rep. of Germany . |
| 850750 | 7/1952 | Fed. Rep. of Germany . |
| 1043342 | 6/1959 | Fed. Rep. of Germany . |
| 2303619 | 8/1974 | Fed. Rep. of Germany . |
| 2461922 | 8/1976 | Fed. Rep. of Germany . |

OTHER PUBLICATIONS

Reppe et al., Annalen der Chemie, vol. 596 (1955), pp. 80–87.

*Primary Examiner*—Richard Raymond
*Attorney, Agent, or Firm*—Keil & Witherspoon

[57] ABSTRACT

Cyclic ethers, especially tetrahydrofuran, are manufactured by dehydrating diols in the liquid phase in the presence of a bleaching earth as the catalyst and of a minor amount of an alkali metal or alkaline earth metal carbonate or bicarbonate.

4 Claims, No Drawings

MANUFACTURE OF CYCLIC ETHERS

The present invention relates to a process for the manufacture of cyclic ethers by dehydrating diols in the presence of a bleaching earth.

Numerous processes of this type, e.g. the dehydration of butane-1,4-diol to tetrahydrofuran (THF), have been disclosed. The state of the art in 1955 has been described in Liebigs Annalen der Chemie, 596 (1955), 81.

The dehydrating agents listed are phosphoric acid, sulfuric acid, oxalic acid, copper sulfate, magnesium chloride, zinc chloride and a plurality of others. Using these acidic compounds, the elimination of water is generally carried out in the liquid phase at up to 250° C. If it is carried out above 250° C., certain other catalysts, e.g. oxides of aluminum, titanium, zirconium and tungsten, and also bleaching earths and phosphates, become active. Since butanediol in particular boils at 245° C., the reaction of this compound is carried out either in the gas phase or under pressure (cf. German Pat. No. 711,709). However, at these relatively high reaction temperatures, a significant degree of butadiene formation is observed.

The numerous processes which have been disclosed suffer from a series of disadvantages. If soluble catalysts are used, there is substantial catalyst consumption and the yield in general does not exceed 90%. Improved processes disclosed subsequently, e.g. the process of German Pat. No. 850,750, where the reaction is carried out by means of a cation exchanger, do not provide any substantial improvement, especially since the commercial exchanger resins have only a short life at reaction temperatures of 150° C. The use of small amounts of concentrated sulfuric acid, as described in German Pat. No. 1,043,342 requires the synthesis to be carried out in apparatus with a corrosion-resistant inner lining, and is therefore relatively expensive. Furthermore, experience has shown that in this method barely more than 10,000 parts of butanediol are converted per part by weight of sulfuric acid; beyond this point, the catalyst proves to have been consumed by impurities and must be destroyed. In doing so, the butanediol still present in the reaction apparatus is also lost. In view of the fact that ethers such as THF are manufactured on a large scale, the amount of catalyst to be destroyed, and the amount of starting material lost at the same time, constitutes a substantial disadvantage.

Attention has been drawn frequently to the possibility of using bleaching earths for the manufacture of tetrahydrofuran (Liebigs Annalen, loc. cit., or, for example, German Pat. No. 700,036). However, a precise description of the process using a bleaching earth as the catalyst has not been given. Merely a process for the manufacture of THF using aluminum and magnesium silicates, has been disclosed in German Laid-Open Application DOS No. 2,461,922. This is a gas phase process and, compared to liquid phase processes suffers, inter alia, from the disadvantage that, for example, the butanediol to be reacted must be vaporized before the actual reaction. Of course, such a process is disadvantageous from the point of view of energy requirement. Furthermore, if butanediol of inferior quality, or a crude product, is employed in the process, the life of the catalyst is low. In addition, the catalyst activity declines very rapidly due to the deposition of polymeric products.

In our investigations of the use of bleaching earths for the manufacture of cyclic ethers we have found that these earths are very active dehydrating catalysts, and, for example, convert butane-1,4-diol rapidly to THF at relatively low temperatures.

It therefore proved a serious disadvantage that these catalysts also convert small amounts of the butanediol (about 0.5%) to a high molecular weight insoluble polymer.

Since bleaching earths are normally only obtainable as fine powders or as small granules, they have to be used in a suspended form. This results in an arrangement in which stirred kettles or similar reaction vessels are used, in which the polymer accumulates and deposits, as a solid, on the walls and heaters. Moreover, the activity of the catalyst very rapidly declines. The catalyst, and the polymer, which is insoluble in all conventional solvents, must be removed mechanically. Of course this is expensive and entails a great deal of shutdown time. This is particularly true where technical, not particularly pure, grades of diols are to be converted to cyclic ethers, since the formation of polymers is found to be particularly pronounced when such diols are used. Possibly the impurities present in the diols are responsible for the formation of the polymer.

It is an object of the present invention to provide a process, and a catalyst based on bleaching earths, by means of which the conversion of diols to cyclic ethers can be carried out without problems, with high yield and with low catalyst consumption and which can in particular also be applied to technical, not particularly pure, diols. In particular, it is important that it should also be possible to use the catalyst with crude aqueous butanediol solutions obtained by hydrogenation of butynediol synthesized by the Reppe process. It is known that non-distilled butanediol produced in this way may contain sodium formate or calcium formate as impurities. German Laid-Open Application DOS No. 2,303,619 describes a relatively troublesome and expensive process for converting such a product to THF, in which the impurities are removed from the reaction system with the aid of tall oil.

We have found that the above object is achieved by using a catalyst consisting of bleaching earth which, according to the invention, is used conjointly with an alkali metal or alkaline earth metal carbonate or bicarbonate. Bleaching earths, also referred to as fuller's earths, are colloidal, water-containing aluminum hydrosilicates of the montmorillonite group, in which the aluminum ions may be partially replaced by iron or magnesium ions. The ratio of silica to alumina in these minerals is about 4:1. They are commercial products which are usually activated by acid treatment and are used extensively for refining edible oils and fats as well as mineral oils.

It is true that if a bleaching earth is used without an alkali metal carbonate or alkaline earth metal carbonate for the manufacture of THF from butane-1,4-diol, cyclic ethers are formed, at a high rate of reaction, in the initial stage of the reaction but after only 1 or 2 days the rate drops to a fraction of its original value. Furthermore, the insoluble polymer referred to above forms. In contrast, if the bleaching earth is used together with the carbonate, no insoluble polymer results and merely the impurities present in the butanediol accumulate, as a bottom product, if the process is carried out in suspension. These impurities can very easily be separated from the catalyst by washing with a solvent, for example methanol.

The amount of alkali metal or alkaline earth metal carbonate or bicarbonate added is from 0.3 to 1.8, advantageously from 0.5 to 1.5, percent by weight based on the weight of the catalyst.

According to the invention, the elimination of water is carried out in the liquid phase using a suspended or fixed catalyst, i.e. in the latter case the bleaching earth is arranged in the form of a fixed bed. The carbonate may be added to the reaction mixture as a solid or in solution.

The novel process gives virtually quantitative yields, has unlimited catalyst productivity, and does not pollute the environment. Since the reaction mixture does not contain any corrosive substances, the production equipment can be made from inexpensive materials, e.g. conventional apparatus steel. The use of lead-lined vessels, which is necessary, and encountered in industrial practice, when the reaction is carried out with sulfuric acid, is not called for in the process of the invention.

The reaction rate depends on the chosen reaction temperature and on the amount of catalyst. For example, at 200° C. up to 20 parts of THF per hour can be produced from butanediol per part by weight of catalyst. The dehydration is carried out at from 140° to 230° C., preferably from 150° to 200° C., in general at conventional pressures, i.e. atmospheric pressure or slightly above or below this value. When working under reduced pressure it is necessary to ensure that the boiling point of the diol should not be lower than the reaction temperature. The amount of catalyst used does not depend on chemical circumstances but on the technological details, for example the achievable distillation rate, the reactor geometry and the like. In general, the catalyst is used as a suspension of from 0.5 to 10 percent strength by weight.

The process is applicable to the cyclizing dehydration of diols. Diols of four or more carbon atoms, especially of 4 to 10 carbon atoms, can be converted to the corresponding cyclic ethers. Accordingly, examples of suitable diols are butane-1,4-diol, but-2-ene-1,4-diol, pentane-1,4-diol, pentane-1,5-diol and hexane-2,5-diol. From an industrial point of view the manufacture of tetrahydrofuran from butane-1,4-diol is particularly important.

In order to stabilize the reaction temperature, the dehydration can also be carried out in the presence of a chemically inert solvent. Examples of suitable diluents are hydrocarbons, e.g. dodecane or gasoline fractions, highboiling ketones or ethers, e.g. decanone or dihexyl ether, and preferably the reaction product itself, though in that case, because of its volatility, it would be necessary to work under superatmospheric pressure. In most cases, the use of a diluent is unnecessary. Minor amounts of water may also be used as a solvent, particularly since water is formed during the reaction.

Whilst the process can be operated batchwise, continuous operation is advantageous. A particularly advantageous method is to add the diol in question to the reaction mixture, whilst stirring, at the same rate as that at which the reaction product distils from the reaction vessel, for example through an appropriate fractionating column. In that case, the material obtained at the top of the column as a rule consists of the pure product together with the water formed and with any water which may have been introduced with the raw material.

In the Example which follows, parts are by weight and bear the same relation to parts by volume as that of the kilogram to the liter.

EXAMPLE

A distillation vessel equipped with a stirrer and surmounted by a fractionating attachment is used. The catalyst, consisting of 50 parts of bleaching earth sold under the name of Tonsil, Optimum FF ® (from Süudchemie, Munich) and 0.65 part of sodium bicarbonate is added to 2,000 parts of butane-1,4-diol and the reaction mixture is heated to 180° C. A vigorous reaction already starts at 150° C. At 180° C., 450 parts of butanediol are converted to THF per hour. The consumed butanediol is replaced by running fresh material into the vessel at the rate of the reaction. After 100,000 parts of butanediol have been converted, the reaction rate is still 150 parts per hour. A further 50 parts of Tonsil and 0.65 part of sodium bicarbonate are then added to the bottom material. Thereupon, the hourly rate of conversion again rises, to about 550 parts of butane-1,4-diol, and a further 100,000 parts of butanediol are converted to THF. Finally, after stopping the feed, the bottom material in the vessel is heated at 180° C. for a further 20 hours, after which the reaction has ended. The residue consists of about 100 parts of inorganic solids and 330 parts of an oily residue which is readily soluble in methanol. The yield is virtually quantitative.

If the same procedure is followed except that the sodium bicarbonate is omitted, the conversion rate is as low as 50 parts of butanediol per hour after only 45,000 parts of butanediol have been processed. A further 50 parts of Tonsil Optimum FF are added. The rate of conversion initially rises to 500 parts of butanediol per hour but after a further 50,000 parts have been reacted, it drops to virtually 0. 400 parts of a solid insoluble polymer remain; this material is very troublesome to remove from the reaction vessel.

A similar result to that described above is achieved if instead of 0.65 part of sodium bicarbonate 0.3 part of sodium carbonate or calcium carbonate is used.

We claim:

1. A process for the manufacture of a cyclic ether by dehydrating a diol of 4 to 10 carbon atoms in the liquid phase over a dehydrating catalyst selected from the group of the bleaching earths, wherein the reaction is carried out in the presence of from 0.3 to 1.8 percent by weight, based on the amount of bleaching earth used, of an alkali metal or alkaline earth metal carbonate or bicarbonate.

2. A process as claimed in claim 1, wherein tetrahydrofuran is manufactured from butane-1,4-diol.

3. A process as claimed in claim 1, wherein from 0.5 to 1.5 percent by weight of the alkali metal or alkaline metal carbonate or bicarbonate are used.

4. A process as claimed in claim 1, wherein the dehydration is carried out at from 140° to 230° C.